(12) United States Patent
Fuchs et al.

(10) Patent No.: US 10,873,164 B2
(45) Date of Patent: Dec. 22, 2020

(54) CONNECTOR

(71) Applicant: Eximis Surgical, LLC, Louisville, CO (US)

(72) Inventors: Robert Fuchs, Louisville, CO (US); Dirk Johnson, Louisville, CO (US); William N. Gregg, Superior, CO (US)

(73) Assignee: Eximis Surgical Inc., Louisville, CO (US)

( * ) Notice: Subject to any disclaimer, the term of this patent is extended or adjusted under 35 U.S.C. 154(b) by 541 days.

(21) Appl. No.: 15/712,436

(22) Filed: Sep. 22, 2017

(65) Prior Publication Data

US 2018/0090889 A1 Mar. 29, 2018

Related U.S. Application Data

(60) Provisional application No. 62/398,726, filed on Sep. 23, 2016.

(51) Int. Cl.
*A61B 18/12* (2006.01)
*H01R 13/72* (2006.01)
(Continued)

(52) U.S. Cl.
CPC ....... *H01R 13/72* (2013.01); *A61B 17/00234* (2013.01); *A61B 18/1445* (2013.01);
(Continued)

(58) Field of Classification Search
CPC .......... A61B 17/00234; A61B 18/1445; A61B 18/1482; A61B 2017/00287; A61B 2017/00398; A61B 2017/00477; A61B 2017/00526; A61B 2017/2212; A61B 2018/00101; A61B 2018/00172; A61B 2018/00178; A61B 2018/00184; A61B 2018/00601; A61B 2018/1407; A61B 2018/141; A61B 2018/144; A61B 2018/1475; H01R 13/42; H01R 13/627; H01R 13/72

See application file for complete search history.

(56) References Cited

U.S. PATENT DOCUMENTS 4,170,393 A * 10/1979 Mocek, Jr. ............. H01R 13/42
439/601
5,611,798 A * 3/1997 Eggers ................. A61B 18/082
219/230

(Continued)

OTHER PUBLICATIONS

Vizzini, Damiano, "International Serach Report and Written Opinion Re Application No. PCT/US2017/053028", dated Dec. 13, 2017, p. 13 Published in: WO.

(Continued)

*Primary Examiner* — Daniel W Fowler
(74) *Attorney, Agent, or Firm* — Neugeboren O'Dowd PC

(57) ABSTRACT

A coupling system and related methods are disclosed. The system has a first plug detachably coupled to a first housing, and a first socket detachably coupled to a second housing. The first socket is configured to receive the first plug. The system is movable between a first configuration wherein the first and second housings are not engaged and a second configuration wherein the first and second housings are engaged and the first plug and the first socket are coupled together.

21 Claims, 23 Drawing Sheets

(51) Int. Cl.
*A61B 18/14* (2006.01)
*A61B 17/00* (2006.01)
*H01R 13/42* (2006.01)
*H01R 13/627* (2006.01)
*A61B 18/00* (2006.01)
*A61B 17/221* (2006.01)

(52) U.S. Cl.
CPC ......... *A61B 18/1482* (2013.01); *H01R 13/42* (2013.01); *H01R 13/627* (2013.01); *A61B 2017/00287* (2013.01); *A61B 2017/00398* (2013.01); *A61B 2017/00477* (2013.01); *A61B 2017/00526* (2013.01); *A61B 2017/2212* (2013.01); *A61B 2018/00101* (2013.01); *A61B 2018/00172* (2013.01); *A61B 2018/00178* (2013.01); *A61B 2018/00184* (2013.01); *A61B 2018/00601* (2013.01); *A61B 2018/141* (2013.01); *A61B 2018/144* (2013.01); *A61B 2018/1407* (2013.01); *A61B 2018/1475* (2013.01)

(56) References Cited

U.S. PATENT DOCUMENTS

| | | | |
|---|---|---|---|
| 7,445,528 | B1 | 11/2008 | Kuzma |
| 2003/0018332 | A1* | 1/2003 | Schmaltz ............ A61B 18/1445 606/51 |
| 2011/0270256 | A1 | 11/2011 | Nelson et al. |
| 2012/0004655 | A1* | 1/2012 | Kim ....................... A61B 18/12 606/41 |
| 2016/0022352 | A1 | 1/2016 | Johnson et al. |
| 2017/0079708 | A1 | 3/2017 | Gilbert et al. |

OTHER PUBLICATIONS

Wittman-Regis, Agnes, "International Preliminary Report on Patentability Regarding International Application No. PCT/US2017/053028", dated Apr. 4, 2019, pp. 8 Published in: WO.

* cited by examiner

CONNECTOR

CLAIM OF PRIORITY UNDER 35 U.S.C. § 119

The present application for patent claims priority to Provisional Application No. 62/398,726 entitled "CONNECTOR" filed Sep. 23, 2016, first named inventor Robert Fuchs, and hereby expressly incorporated by reference herein in its entirety for all proper purposes.

BACKGROUND

Field

The present invention relates generally to a connector, and more specifically to a connector for attaching medical device components.

Background

Applicant has developed a large volume tissue removal device and method for extracting a tissue specimen from a patient. The method involves placing a retrieval bag about the tissue specimen, segmenting the tissue specimen, and removing the segmented tissue. There remains a need, however, for a suitable connector and method for coupling components of the device.

SUMMARY

An exemplary coupling system has a first plug detachably coupled to a first housing, and a first socket detachably coupled to a second housing, the first socket configured to receive the first plug. The exemplary system is movable between a first configuration wherein the first and second housings are not engaged and a second configuration wherein the first and second housings are engaged and the first plug and the first socket are coupled together.

An exemplary instrument has an actuation tool having a tensioning mechanism, at least one wire, and a coupling system for coupling the tensioning mechanism and the wire. The coupling system has a first plug detachably coupled to a first housing, and a first socket detachably coupled to a second housing, the first socket configured to receive the first plug. The coupling system is movable between a first configuration wherein the first and second housings are not engaged and a second configuration wherein the first and second housings are engaged and the first plug and the first socket are coupled together. The first plug or the first socket is coupled to the at least one wire. The other one of the first plug or the first socket is coupled to the tensioning mechanism.

An exemplary method includes providing a coupling system, the coupling system having a first plug detachably coupled to a first housing, and a first socket detachably coupled to a second housing, the first socket configured to receive the first plug. The exemplary method includes moving the coupling system between a first configuration wherein the first and second housings are not engaged and a second configuration wherein the first and second housings are engaged and the first plug and the first socket are coupled together.

DETAILED DESCRIPTION

As previously described herein, Applicant has developed a large volume tissue removal device and method, which is disclosed in U.S. Patent Pub. No. 2016/0022352A1, published on Jan. 28, 2016, and incorporated herein by reference in its entirety for all proper purposes.

Figure 1:
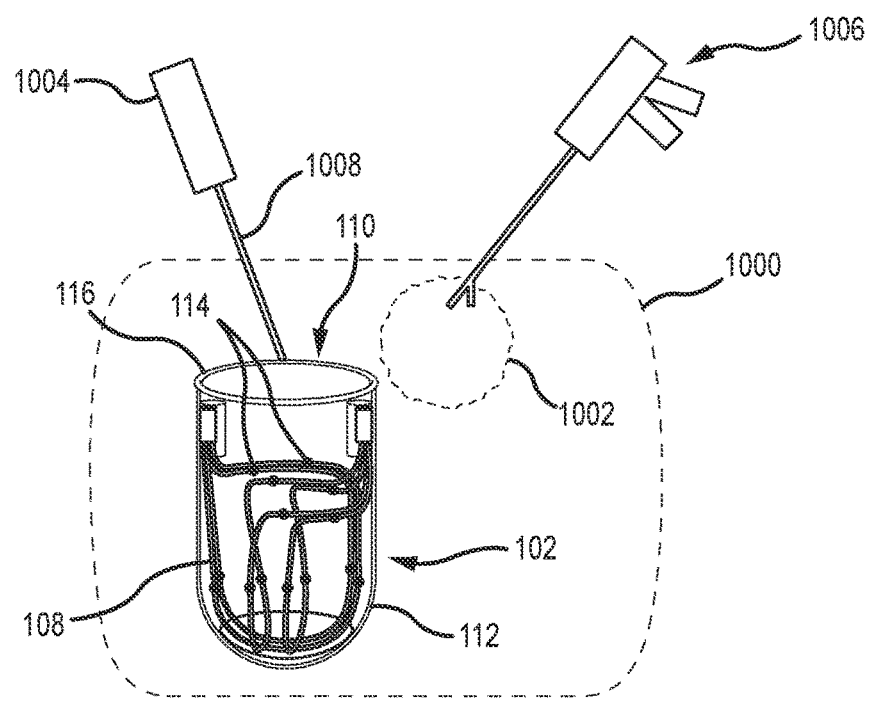
FIG. 1 is a schematic view of a tissue specimen being placed in a specimen removal bag.

Illustrated in FIG. 1 is a retrieval bag 102 according to some embodiments, deployed inside a cavity 1000 of a patient. The retrieval bag 102 is shaped and sized so as to receive a tissue specimen 1002 that is being surgically removed from the cavity 1000. Those of skill in the art will understand how to select the appropriate sizing of the retrieval bag 102 in relation to the particular tissue specimen 1002 being removed.

In the embodiment shown, the retrieval bag 102 has a container 112 with an entry 110, and a plurality of electrodes 108 disposed in the container 112. The container 112 may be flexible and deployable through a standard surgical tube, such as a cannula or lumen, as is known in the art. In some embodiments, a fastener 114 or a plurality of fasteners 114 may be provided to temporarily or permanently fasten the electrodes 108 to the container 112 in a desired configuration.

A spring-biased ring 116 may be provided at the entry 110 of the retrieval bag 102 to ease the opening of the retrieval bag 102; however, those of skill in the art will understand that this is not necessary to practice the invention. In some embodiments, the container 112 and the fasteners 114 are configured to be deployed through a tube 1008, such as through a deployment instrument 1004, into the cavity 1000 and allowed to spring into place.

After the retrieval bag 102 is in place, a grasper 1006 or any means known in the art may be provided to manipulate the specimen 1002 into the retrieval bag 102 prior to removal from the patient. Those of skill in the art will understand how the surgical team might loosen the specimen 1002 and move it into the retrieval bag 102.

Figure 2:
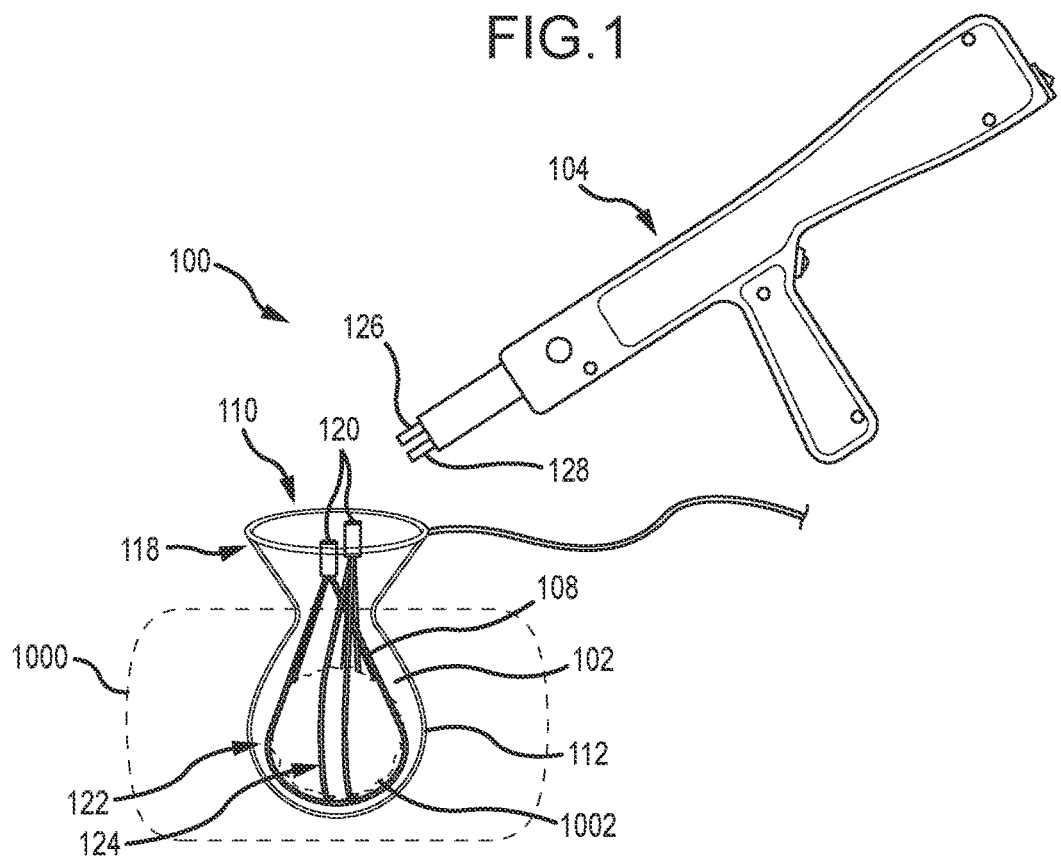
FIG. 2 is a schematic view of a surgical device having an exemplary connector.

Turning now to FIG. 2, illustrating a retrieval device 100, a proximal portion 118 of the retrieval bag 102 and respective proximal portions 120 of the electrodes 108 may be exteriorized, that is, pulled out of the cavity 1000 such that a surgeon can access the proximal portion 118 of the retrieval bag 102 and the proximal portions 120 of the electrodes.

In some embodiments, the proximal portions 120 of the electrodes 108 are pre-crimped to facilitate attachment to an actuator 104 although those of skill in the art will understand that this feature is not necessary.

In some embodiments, a first set 122 of electrodes 108 is crimped or otherwise coupled at the proximal portions 120 to facilitate attachment to a first actuator rod 126. Similarly, a second set 124 of electrodes 108 may be crimped or otherwise coupled at the proximal portions 120 to facilitate attachment to a second actuator rod 128. Those of skill in the art will readily envision any number of means for attaching the electrodes 108 to the actuator 104, all of which are contemplated.

Figure 3:
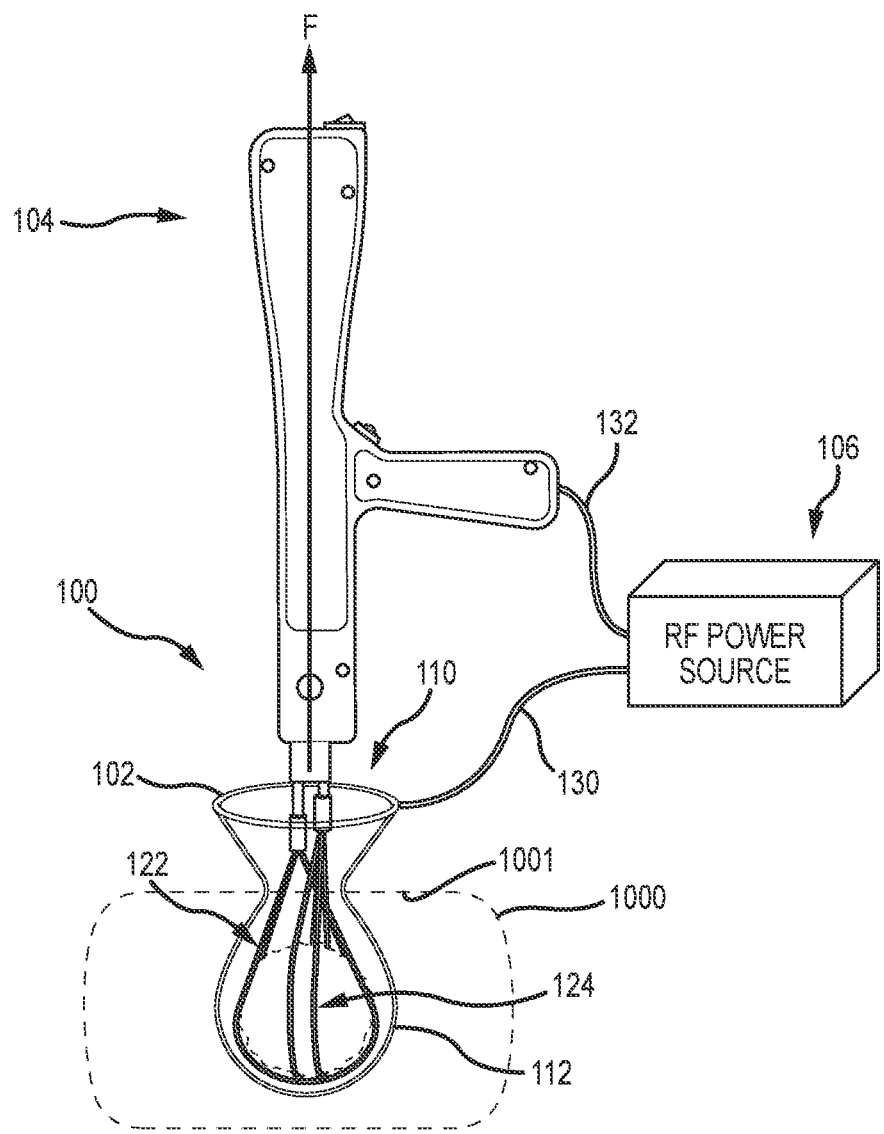
FIG. 3 is another schematic view of the surgical device in FIG. 2.

In some embodiments, and as illustrated in FIG. 3, a proximal force F may be applied to the electrodes 108 to initiate and/or maintain a tissue segmentation operation. Those of skill in the art will understand that an opposing force is necessary to maintain the actuator 104 and retrieval bag 102 in a stable position.

In some embodiments, portions of the retrieval bag 102 containing the specimen 1002 and electrodes 122, 124, 108 are configured to not contact the interior wall 1001 of the cavity 1000. In some embodiments, a distal insertion tube (not illustrated) is provided, against which the specimen 1002 may abut while the electrodes 108 are being pulled through the specimen 1002. In some embodiments, an additional thermal barrier (not shown) is provided in a wall of the retrieval bag 102 or on an exterior surface of the retrieval bag 102 so that any contact with the cavity 1000 will be protected from thermal damage. The thermal barrier may include a thermally insulative layer or a feature that can be inflated with air or a fluid (not illustrated). In some embodiments, the surgeon may use a laparoscopic camera to visually ensure that no contact is being made with the interior body cavity 1000.

Continuing with FIG. 3, in some embodiments, after the exteriorizing of the retrieval bag 12, an actuator 104 may be coupled to the proximal portions 120 of the electrodes 122, 124, 108. As will be understood by those skilled in the art, a generator 106, such as a radio frequency (RF) power source may be coupled to the actuator 104, and a return electrode 130 may be coupled to the retrieval bag 102, if one was not previously provided. The tissue removal device 100 is illustrated in FIG. 1 in a ready-state for tissue segmentation.

Figure 4:
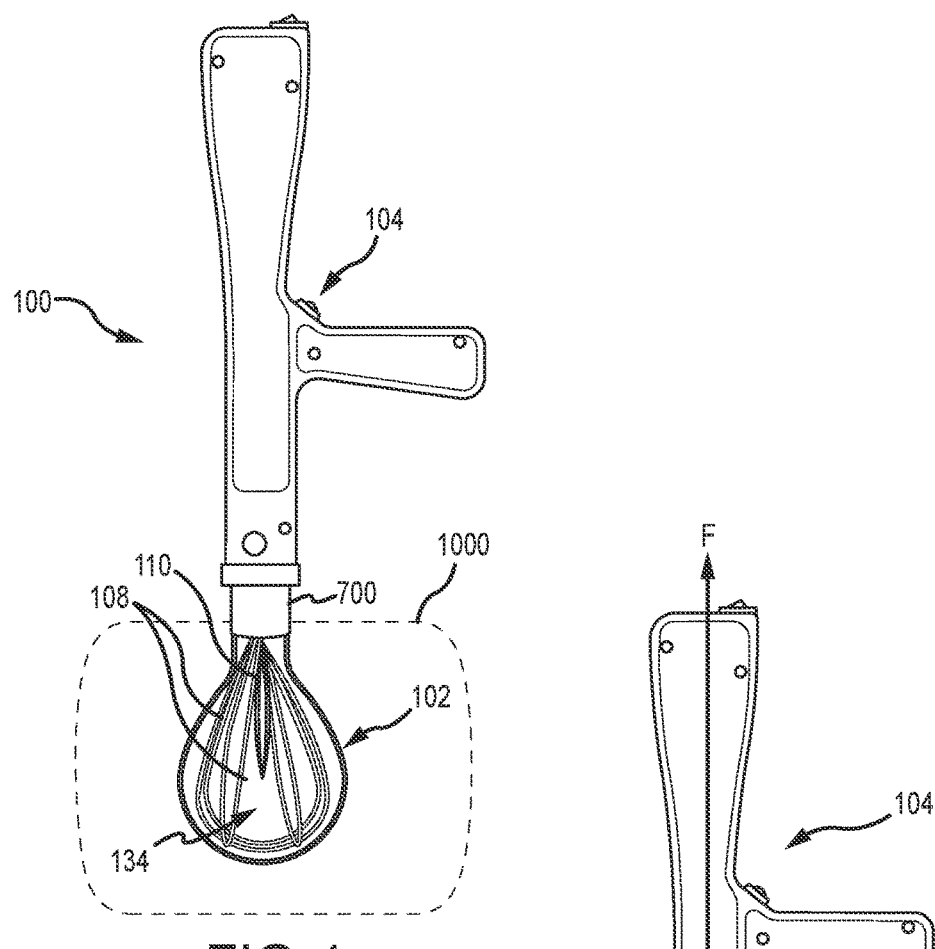
FIG. 4 is a schematic view of a surgical instrument.
Figure 5:
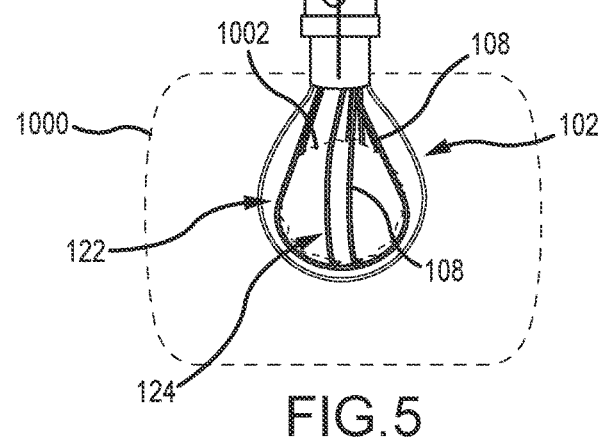
FIG. 5 is another schematic view of the instrument in FIG. 4.
Figure 6:
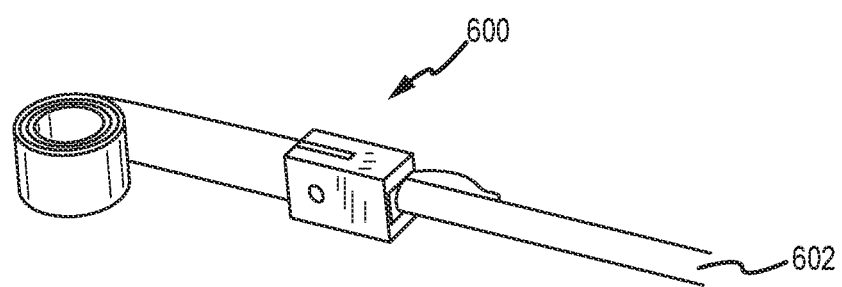
FIG. 6 is a perspective view of a tensioning mechanism suitable for use in a surgical instrument.

Turning now to FIGS. 4-6, in some embodiments, the tissue removal device 100 includes a retrieval bag 102 and actuator 104 that are coupled or assembled together prior to insertion into the cavity 1000 and/or placement of the specimen 1002 inside the retrieval bag 102. For example, the tissue removal device 100 may have a retrieval bag 102 and an electrode 108 or electrodes 108 that are biased to expand upon deployment inside the cavity 1000, or remain expanded upon being forcibly expanded by, for example, a grasper 1006, such that the retrieval bag 102 and the electrode(s) 108 provide a receiving space 134 for a specimen 1002. The retrieval bag 102 may have an entry 110 that is generally to a side of the retrieval bag 102 as illustrated, such that transverse movement of the specimen 1002 allows the specimen 1002 to be placed inside the retrieval bag 102. In some embodiments, the entry 110 may be a longitudinal slit in the retrieval bag that may be pulled open by a biasing effect of the electrodes 108, forcibly opened as a user forces the electrodes 108 into a spaced-apart configuration, and/or a user pushing the specimen 1002 into the entry 110. The entry 110 may be biased towards a closed configuration, and/or the entry 110 may be sealable using means known to those of skill in the art. In some embodiments, actuation of the actuator 104 may cause the electrodes 108 to move towards each other and thereby sealing the entry 110 and/or causing opposing portions of the entry 110 to overlap to effectuate a barrier between the specimen 1002 and the cavity 1000. In some embodiments, causing the electrodes 108 to apply a proximal force F on the specimen 1002 may cause the retrieval bag 102 and entry 110 to draw into the actuator 104 to effect a closure of the entry 110 or a barrier between the specimen 1002 and the cavity 1000. In some embodiments, the actuator 104 is attached to the retrieval bag 102 prior to deployment into the cavity 1000.

As illustrated in FIG. 5, the entry 110 of the retrieval bag 102 may be exteriorized as the actuator 104 applies a proximal force F to the electrodes 108. The proximal force F may also substantially simultaneously cause the retrieval bag 102 and electrodes 108 to contract or move inwardly to surround the specimen 1002 and effectuate a desired surrounding of the specimen 1002 and/or a desired electrode configuration or pattern relative to the specimen 1002. In some embodiments, a mechanical operation such as manipulation of a switch or lever may be performed so as to effectuate a retraction of the electrodes 108 and proximal force F on the tissue specimen 1002.

In some embodiments, and as illustrated in FIG. 3, after the retrieval bag 102 is exteriorized, a generator 106 may be attached to the actuator 104 so as to allow energy to be applied to the electrodes 108. Attaching the generator 106 may include coupling a power source line 132 and a return electrode 130 in a manner known to those skilled in the art.

The tissue specimen removal device 100 and related methods may include a combination of mechanical and electrical connections to be made during the surgical procedure from electrodes/wires 108 in the specimen bag 102 to the tensioning mechanism or actuator 104 in the segmentation instrument. The device 100 requires that after connection, the wires 108 be able to conduct RF energy while they are being retracted into the segmentation instrument 104 with each contact and its wire set being able to travel independently of the other wire sets.

Figure 7:
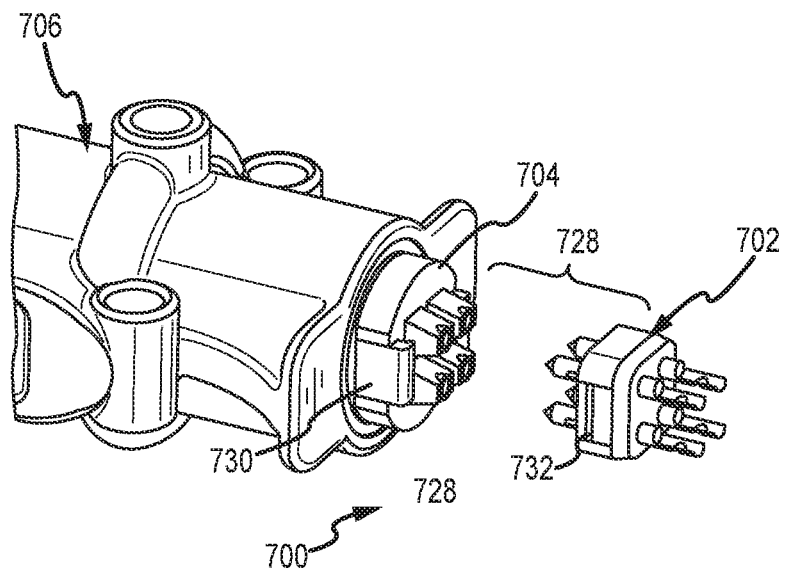
FIG. 7 is a perspective view of a coupling system suitable for use in a surgical instrument.

Turning now to FIG. 7, a coupling system 700 suitable for coupling the wires 108 and instrument 104 previously described herein is now described in further detail.

The coupling system 700 may include a first plug 714 detachably coupled to a first housing 710, and a first socket 716 detachably coupled to a second housing 712. The first socket 716 may be configured to receive the first plug 714. Those skilled in the art will recognize that, although the housing 712 is illustrated as a separate component from the tool 706 in FIG. 7, in some embodiments, the housing 712 and actuation tool 706 may be unitary and/or permanently coupled.

Figure 8:
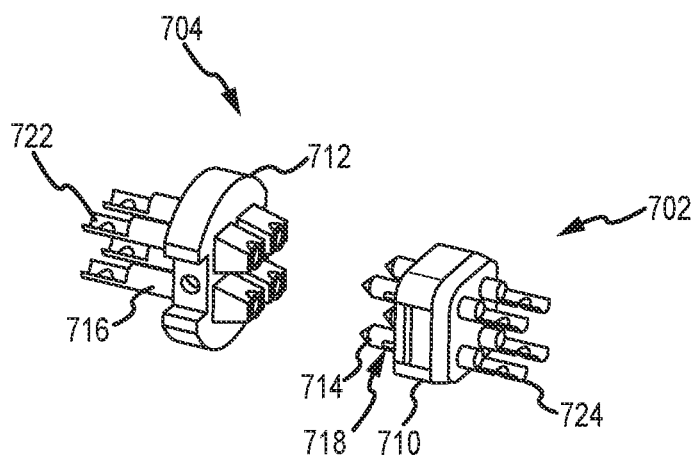
FIG. 8 is a perspective view of some components of the coupling system.
Figure 9:
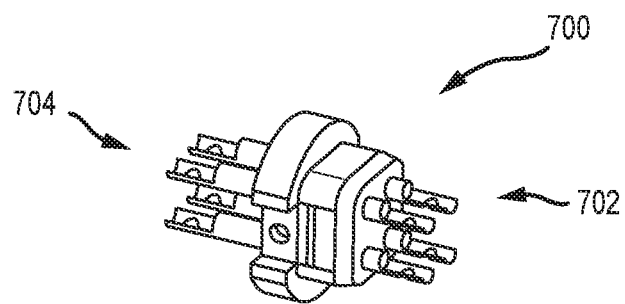
FIG. 9 is a perspective view of some components of the coupling system.

As illustrated in FIGS. 8 and 9, the coupling system 700 may be movable between a first configuration wherein the first and second housings 710, 712 are not engaged (see FIG. 8) and a second configuration wherein the first and second housings 710, 712 are engaged and the first plug 714 and the first socket 714 are coupled together.

As seen most clearly in FIG. 7, the coupling system 700 may include a retaining mechanism 728 for locking the first and second housings 710, 712 in the second configuration. The retaining mechanism 728 may include a lock member 730 in one of the housings 710, 712, and a catch 732 in the other housing 710, 712. The lock member 730 and the catch 732 may selectively maintain the first and second housings 710, 712 in the second configuration. For example, the retaining mechanism 728 may provide a detent engagement between the lock member 730 and the catch 732, a manual lock member 730. Those skilled in the art will readily recognize that the coupling system 700 may include a retaining means that includes any retaining means for providing a non-permanent engagement between the first and second housings 710, 712 may be provided. When the system 700 is in the first configuration, the first plug 714 may be fixed relative to the first housing 710 and the first socket 716 may be fixed relative to the second housing 712. A friction fit may maintain the plug 714 and the socket 716 fixed, respectively, to the first and second housings 710, 712.

Figure 10:
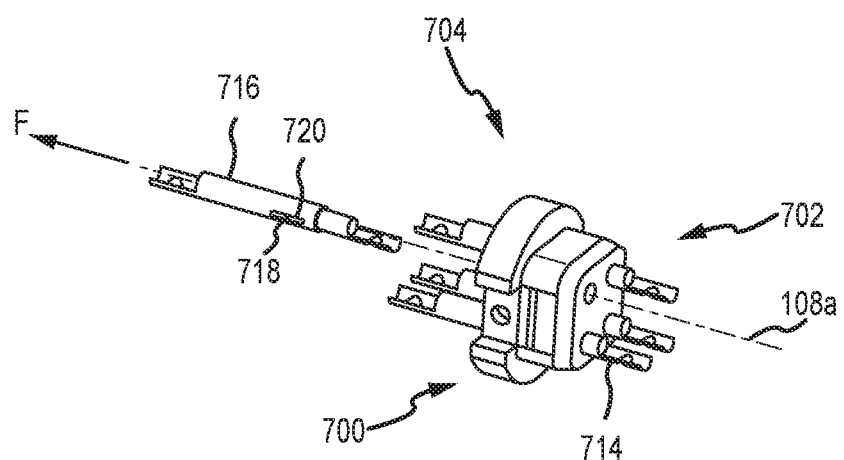
FIG. 10 is a perspective exploded view of some components of the coupling system.

As illustrated most clearly in FIG. 10, when the coupling system 700 is in the second configuration, the first plug 714 and the first socket 716 may be slidable relative to the first and second housings 710, 712.

In some embodiments, the plug 714 and socket may be slidable when the system is in the second configuration, by the application of a pulling force F (see e.g. FIG. 10) that is greater than a retaining force applied by the friction fits of the first plug 714 and first socket 716.

In some embodiments, the first plug 714 and the first socket 716 may be coupled together by a detent engagement. In some embodiments, a resilient protruding portion 718 (see FIG. 8) on the plug 714 and/or the socket 716 may be provided, so as to engage a recess 720 (see e.g. FIG. 10) in the other one of the plug 714 and/or socket 716.

Figure 14:
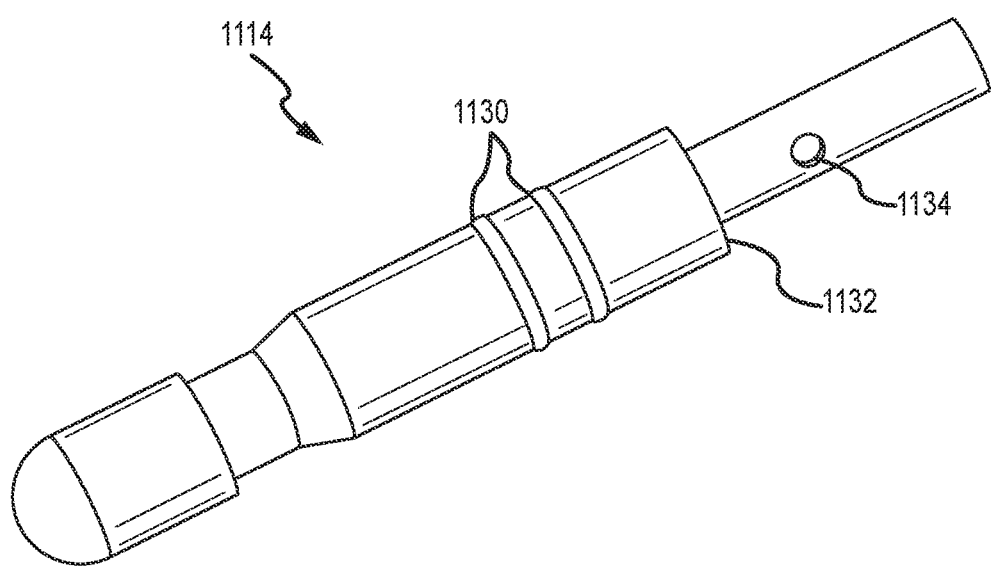
FIG. 14 is a perspective view of a plug suitable for use in the instrument in FIG. 11.

As illustrated in FIG. 14, in some embodiments, the coupling system 700 may have an alignment mechanism 738 configured to align the first plug 714 and the first socket 716. The alignment mechanism 738 may include a protrusion 740 in one of the housings 710, 712 and a recess 742 in the other one of the housings 710, 712. Those skilled in the art will recognize that the protrusion 740 and/or recess 742 may have ramped surfaces so as to guide the housings 710, 712 into the correct orientation, thereby aligning the plug 714 and socket 716 prior to engagement of the plug 714 and socket 716.

Figure 20:
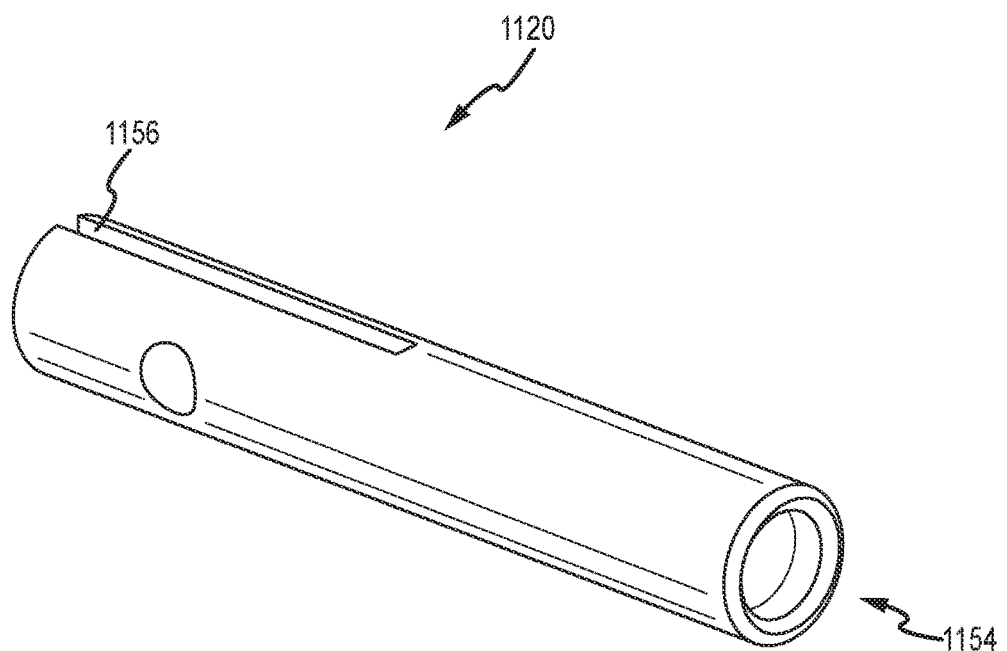
FIG. 20 is a perspective view of a socket suitable for use in the instrument in FIG. 11.
Figure 21:
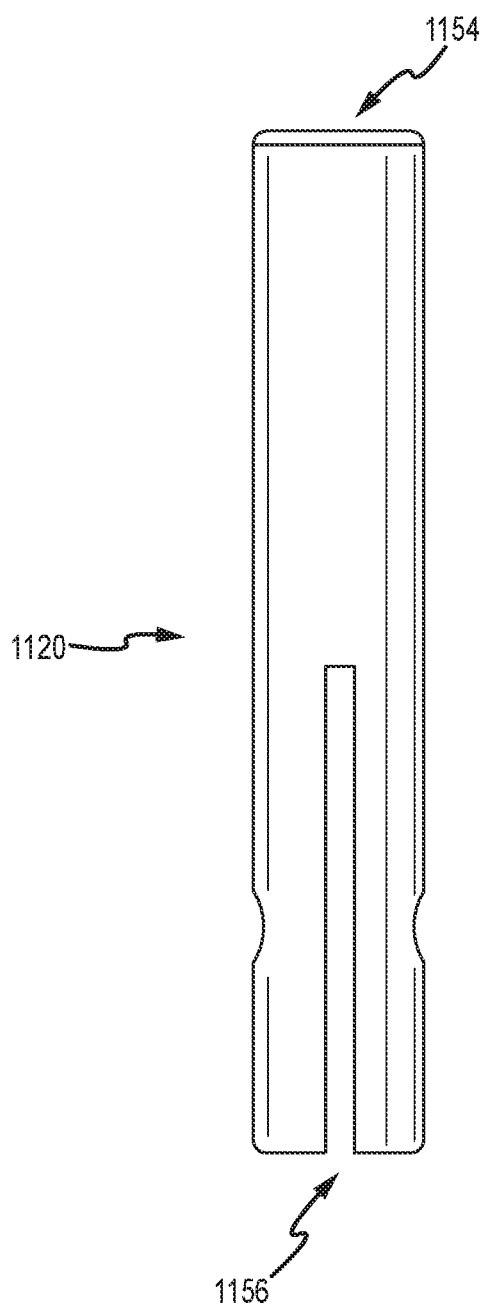
FIG. 21 is a top view of the socket in FIG. 20.
Figure 22:
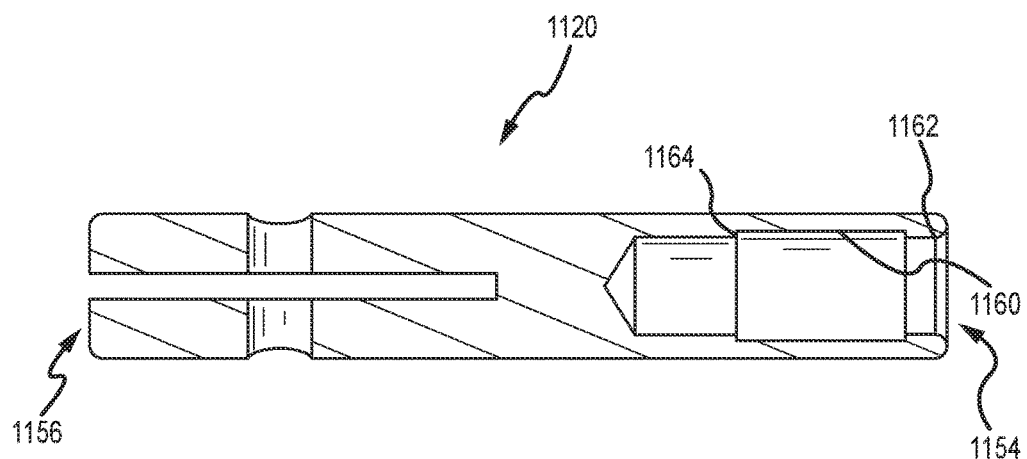
FIG. 22 is a side section view of the socket in FIG. 20.
Figure 23:
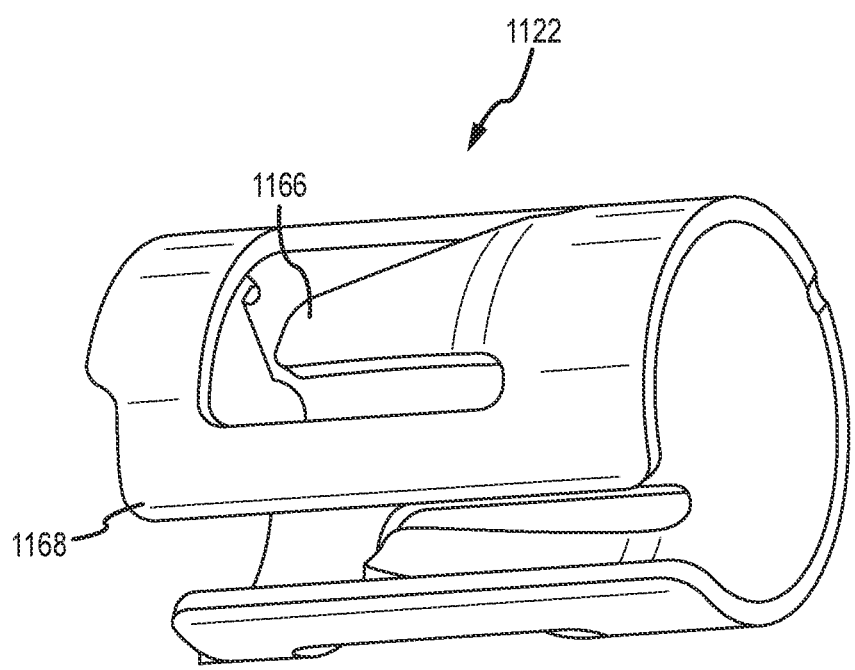
FIG. 23 is a perspective view of a retaining mechanism suitable for use in the instrument in FIG. 11.

As illustrated in FIG. 4, in combination with FIGS. 7-14, in some embodiments, a surgical instrument 100 is provided. The surgical instrument 100 may have an actuation tool 104 having a tensioning mechanism 600 (see e.g. FIG. 6). The tensioning mechanism 600 may have a distal end 602 (see also socket 1112 and receptacle 1154 in FIG. 20), which may be configured to couple to the socket 716 using any suitable means including, but not limited to, a detent engagement, a permanent coupling, a unitary system, a pin and receptacle, clip, etc. The tensioning mechanism 600 may be configured to apply a pulling force F on the socket 716 (see e.g. FIG. 10). The surgical instrument 100 may include at least one wire 108, which may be a wire electrode, and a coupling system 700 for coupling the tensioning mechanism 600 and the wire 108. The coupling system 700 may be as previously described herein. The first plug 714 or the first socket 716 may be coupled to the at least one wire 108, and the other one of the plug 714 or socket 716 may be coupled to the tensioning mechanism 600.

In some embodiments, the plug 714 may be a unique pin or bullet shaped contact 714 within the connector housing 710. The housing 710 may be made of plastic or other non-conductive material. The connector 702 may be selected or configured such that, after the connection is made between the two mating parts of the connector set 702, 704, the socket or contact(s) 716 on the tensioning mechanism side (e.g. the second housing 712) capture the bullet shaped plug(s) contact(s) 714 in the specimen bag side (e.g. the first housing 710) in a manner that will mechanically and electrically couple to the bullet shaped contact 714. The male contacts 714 may be sized to fit just inside of their respective female contacts 716. The male contacts 714 may be designed with a retainer clip or detent or resilient protruding portion 718 at the proximal, segmentation instrument side, of the tip of the contact that would pass through the female contact shaft and secure to a recess (not shown) on the far, proximal end of the female contact tube 716 such that the male contact could not be retracted back out of the female contact after connection. Those skilled in the art will recognize of course that the detent, clip or resilient protruding portion 718 can be designed with a mechanical override if desired.

In order to prevent the male contact or plug 714 from pushing back distally out of the back of the housing 710, a second, or multiple, indent, detent, clip, or catch may be stamped or machined into the shaft of each contact or plug 714. The detent, indent, or clip may make contact with an interior surface of the non-conductive housing 710 allowing only one-way travel, keeping it from progressing in the distal direction. In some embodiments, the opening or shaft of the male contact housing 710 has a reduced diameter "shelf" or shoulder at its distal end, sized somewhat smaller than the diameter of the male contact or plug 714, preventing the male contact from sliding in one direction but allowing the connected wires to pass through.

Figure 13:
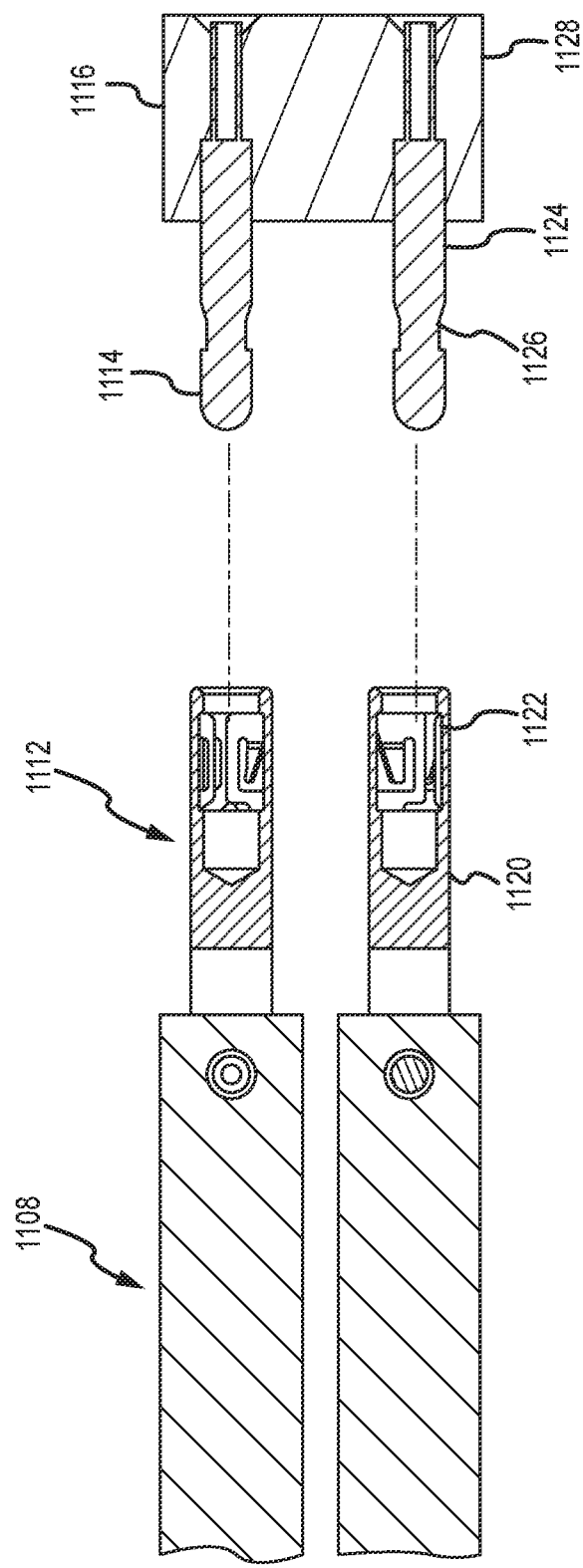
FIG. 13 is a section view of some components of the instrument in FIG. 11.

In some embodiments, the segmentation instrument side of the coupling system 700 may have one or more, female contacts or sockets 716 built into the non-conductive housing 712 of the connector 704 and fixed to the tip of a tensioning mechanism (not illustrated, see e.g. FIG. 6, FIG. 13). The terminal, proximal end of these female metal contacts 716 may have an extension or proximal end 722 that is mechanically connected to the distal end of the tensioning mechanism by way of a weld, rivet, screw, pin or other means of securing the contact extension to the tensioning mechanism.

The housing 712 may hold the female contact 716 in place by friction between the contact 716 and a housing wall. The geometry of the connector housing 712 may be configured such that the friction retaining the contact 716 will be a larger force than the force required to mate the connectors 704, 702, but lower than the force applied by the tensioning mechanism to pull wires 108 through. In this manner, the contacts 716 may remain in place during the connector mating process and release when the tensioning force is applied. The rigid nature of the extended tensioning mechanism may also prevent the female contact 716 from moving in a longitudinal direction until the spring is activated.

The specimen bag side of the connector 702 may have one or more, male contacts 714 built into a non-conductive housing 710 that will align with the contacts 716 on the segmentation instrument side of the connector. The distal ends 724 of the male contacts 714 may be designed in multiple ways to allow connection to their wires 108 (not illustrated in FIG. 10, see e.g. path of travel 108a in FIG. 10), including a crimp, a clamp, soldered or weld. The wires 108 located in the specimen bag 102 (see e.g. FIGS. 1-6) may be terminated in these male contacts 714.

The housings 710, 712 may align and hold the contacts 714, 716 so that the capture of the contacts 714, 716 can occur reliably. When the tensioning force is applied to the desired pair of contacts within the connector housing 712, both housings 710, 712 may stay in place at the connection location held with features in the segmentation instrument while the contact pair 714, 716 and their connected wires 108 travel through the housing and into the instrument. In this manner, the pair of contacts 714, 716 (male and mated female contacts), that have the mechanical tensioning load and the electrical power or RF energy applied may travel through the connector housings 710, 712 and into segmentation instrument as the tissue cutting is performed, while the remaining pairs of contacts are held in the initial contact location.

In some embodiments, a bullet shape of the male contact improves the ability of the mating female contact to align and surround the male contact. For the example, the bullet shaped contact in the specimen bag is assumed to be the male contact and the tensioning instrument is assumed to be the female contact that surrounds the bullet shaped contact. This arrangement can be reversed and the shape of the male contact can be any shape that helps align the two contacts as they are mated, such as a conical shape, a flat ramp or any other geometry that brings the contacts closer to alignment as the connection is made.

As mentioned for the female contact, it may be advantageous to hold the male contact 714 with a frictional force to keep it from extending out of its connector housing before being mated. The frictional force may be selected or configured to be below the tensioning force applied so that it released from the housing when the tensioning mechanism applied the force.

In some embodiments, the contacts 714, 716 are held into the respective housings 710, 712 with retainer clips, detents, springs, stamped features, machined features and/or other extensions and/or surfaces that can catch into recessed or raised surfaces or other features that act as shoulders. The method of retaining the contact(s) 714, 716 can include providing a force that is above the force required to mate the connectors 702, 704, but will release or fail at the force applied by the tensioning mechanism. An advantage of using a clip or other extension to hold the male pin into the housing is that the wire termination can be made to the contact and the terminated contact assembly can be inserted into the back of the housing until the clip or other extension secures the contact in place, making it easier to manufacture.

In some embodiments, the male and female contacts 714, 716 are held into their respective housings 710, 712 with a retaining clip, detent, springs, stamped features, machined features or other extensions and/or surfaces as previously described, but are also designed such that near the most distal end of the female contact, near the end of travel during the mating process, a shape of the male contact causes the method of retaining the female connector in the housing to release. At this point, the female contact has captured the male contact and is now free to move out of the housing with the tensioning mechanism. This release can be integrated into the means of retaining the female contact in the housing and may act like an ejection or release mechanism. It can also be a separate feature that travels into the retention mechanism and causes the retaining mechanism to release, such as a concentric tube that is advanced from the back of the segmentation instrument housing that has an inside diameter that is larger than the mated contact diameter and an outside diameter that will collapse the retaining spring, clip or extension.

Some embodiments allow a fixed orientation of contacts during mating that can independently move with the tensioning mechanism, and may have one of the two connector housings composed of separate pieces. The male contact(s) 714 may be positioned toward the specimen bag and may have a single housing 710 that contains one or more contacts. The contacts may extend outward from the housing but be retained such that they cannot retract out of the back of the housing. The female contact(s) 716 may be positioned toward or attached to the tensioning mechanism (not illustrated) of the segmentation instrument and may have a housing that has multiple pieces, one for each female contact. The multiple pieces are held together by an outer ring or geometry that keeps them oriented together.

A single or multiple set of clips or catches may provide a temporary surface that is positioned at the proximal end of the housing, or at some other position along the length of the connector housing. The clip(s) may fit into a recessed or raised surface in the multiple housing pieces and would retain them from advancing in the proximal or distal direction. The process of mating the connector may compress or extend the retaining clips or catches or otherwise cause the retaining surface to release, thereby allowing the multiple housing pieces to be free to retract proximally out of the outer ring or geometry when the tensioning mechanism applies the force.

In some embodiments, the male contact housing is constructed of separate pieces as described for the female housing above such that both male and female contacts travel with their respective housing into and along the segmentation instrument.

Those skilled in the art will recognize that the embodiments described can be used for a single contact pair connector, a connector with any number of contact greater than one pair. Although the examples of embodiments described include a specimen bag to segmentation instrument application, the embodiments may apply to any application in which the connection of one or more contacts must be made and the contacts allowed to release through the back of one side of the connector housing.

For the connector located within a specimen bag, it is important that it does not have sharp edges that could damage the bag. To reduce the chance of sharp edges the edges on the housing may be beveled, chamfered or rounded. Also, to protect the bag from the tips of the exposed male contacts, wings or walls may be included in the housing to extend beyond the tips of the contact. These walls may fit on the outside of the opposing housing.

In order to ensure that each male contact of the connector mates with its intended female counterpart contact, each housing may be designed with polarized, keyed features that prevent misalignment. Both housings may also have mated retainer snaps, clips or features to ensure the housings do not separate after connection. The segmentation instrument housing may be held in place at the end of the handheld device tray by mated snap on retainer clips, welding, or screws, or may be designed as part of the instrument housing.

The specimen bag side of the connector may include a removable cover to minimize ingress of liquid, bodily fluids or tissue from the specimen bag. This cover may be incorporated into a mounting device intended to mount the connector to the side of the specimen bag. The cover may have the added benefit of protecting the bag from the tips of the male connectors.

The cover may include a flap (not illustrated) that is formed to surround the connecting system 1110 or plugs 1114 (see e.g. FIG. 12) that allows easy access to the connector, may be a semi-permanent layer that covers the connector and requires an intentional user action to remove or release the cover such as with a perforated layer that is torn away from surrounding structure or a rigid component that is placed over the connector that requires user action to unlock or release the cover thus exposing the connector.

In some embodiments, alignment features may be integrated into the segmentation instrument or other handheld device. These alignment features may be molded, machined or added components that hold the female contacts or receptacles in a manner that aligns the male contacts during connection. These features perform the same function as a connector housing and eliminate the need for a separate housing around the female receptacles.

In some embodiments, the mating contacts in one or both connectors may be retained by a temporary retainment friction fit, ring, or other feature that requires more force to overcome than the force to mate the male and female contacts. As such, each mated pair of contacts can only overcome this temporary retainment feature within the connector housing or housings after the pair is mated and can then slide further into the connector to a hard stop retainment feature, thus allowing all male and female contacts to effectively mate when the connectors are brought together.

Those skilled in the art will recognize that the coupling system 700, 1110 previously described is not limited to tissue specimen removal, and may be used in areas outside of tissue specimen removal, such as where a wire, catheter or other types of flexible electrodes may require an electrical connection that remains electrically coupled while the electrode is retracted through a connector housing. Examples may be looped electrodes for amputation of the cervix, endoscopic RF snares or loops, cardiac monitoring and/or ablation catheters, neurological stimulator catheters or other devices where placement of the electrode prior to connection with subsequent retraction is desired.

In addition, the coupling system previously described herein is not limited to applications that use an electrical coupling or connection, and may apply to embodiments where a mechanical coupling that is created by the connector is used to pass the contact and mechanical wire or loop through the connector housing.

Turning now to FIGS. 11-26, a tool such as an instrument 100, 1100 and coupling assembly 1110 are described in further detail. Where a feature is not described, the reader should assume that features and the previous description apply to the following passages.

Figure 11:
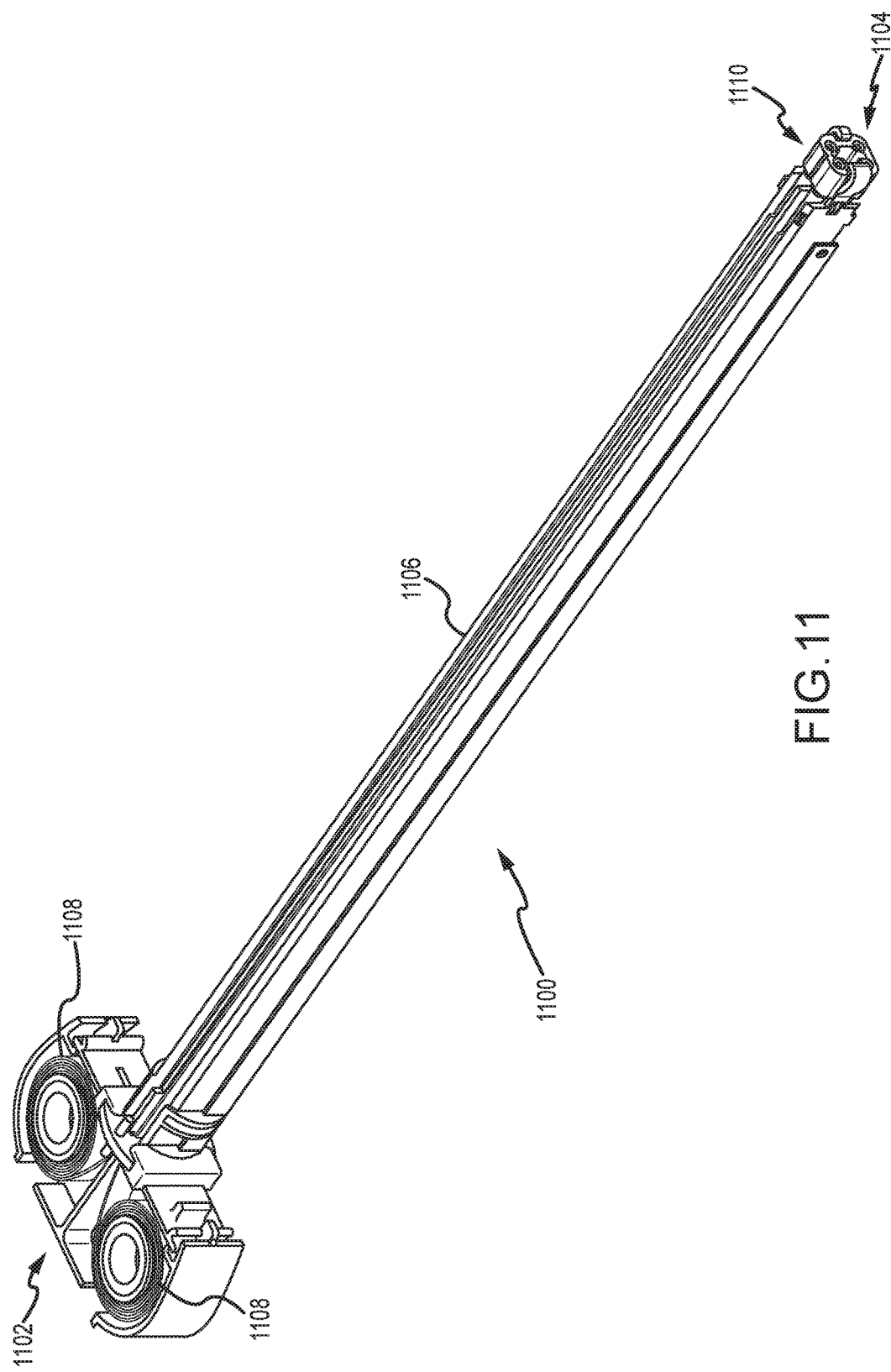
FIG. 11 is a perspective view of an instrument suitable for use in the device illustrated in FIGS. 1-4.

In FIG. 11, an instrument 1100 having a proximal end 1102 and a distal end 1104 has a tray 1106 supporting a plurality of tensioning mechanisms 1108, such as four tensioning mechanisms 1108. The tensioning mechanisms 1108 may be configured to selectively pull a plurality of wires or electrodes (not illustrated in FIG. 11; see wires 108 in FIG. 1) coupled at the distal end, for use in, for example, a tissue removal device.

The wires may be coupled by way of a coupling system 1110, 700.

Figure 12:
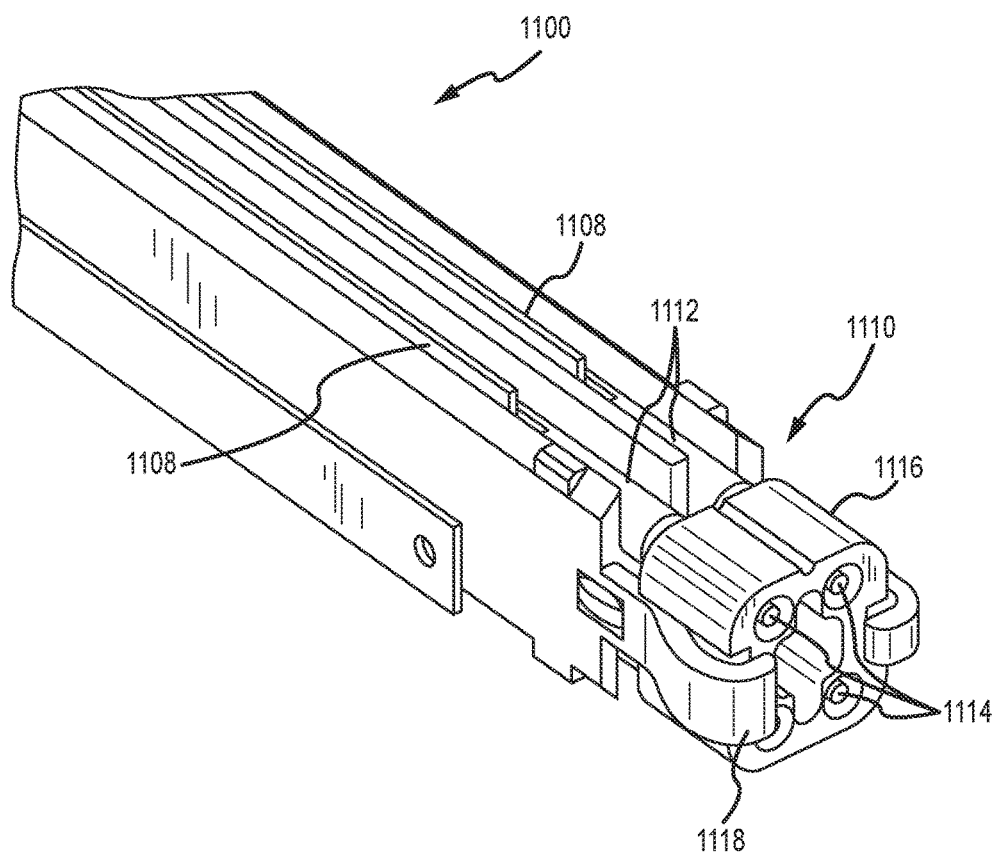
FIG. 12 is a perspective detailed view of the instrument in FIG. 11.

With reference now to FIG. 12, distal ends of the tensioning mechanisms 1108 may be coupled to or unitary with a plurality of sockets 1112. Distal ends of the sockets 1112 may receive proximal ends of a plurality of plugs 1114 positioned in a housing 1116 of the coupling system 1110. Although not illustrated in FIG. 12, the sockets 1112 may be retained by a housing. As previously described herein, the plugs 1114 may be connected to or configured to connect to wires 108 of an electrosurgical instrument.

In some embodiments, the instrument 1100 or tray 1106 has a retaining mechanism 1118 which may include a resilient member on the tray 1106 that selectively engages a recess in the housing 1116, such as by pressing a distal end of the tray 1106 against the housing 1116. The retaining mechanism 1118 may function substantially similarly to the retaining mechanism 728 previously described herein. Those skilled in the art will recognize that a detent or other means for coupling the proximal portion of the instrument 1100 to the distal portion of the instrument 1100 may be provided.

With reference now to FIG. 13, which illustrates details of the instrument 1100, one or more of the sockets 1112 may have a body 1120 coupled to a tensioning mechanism 1108 and housing a plug retaining mechanism 1122 for receiving and retaining a proximal portion of a plug 1114.

One or more plugs 1114 may have a plug body 1124 retained in a housing 1116. The housing 1116 may have a body 1128. The plug(s) 1114 may be retained in the housing 1116 by a friction fit engagement with the housing body 1128. The plug(s) 1114 may have a recess or socket engagement mechanism 1126 for engaging the socket 1112, such as at the plug retaining mechanism 1122.

Figure 15:
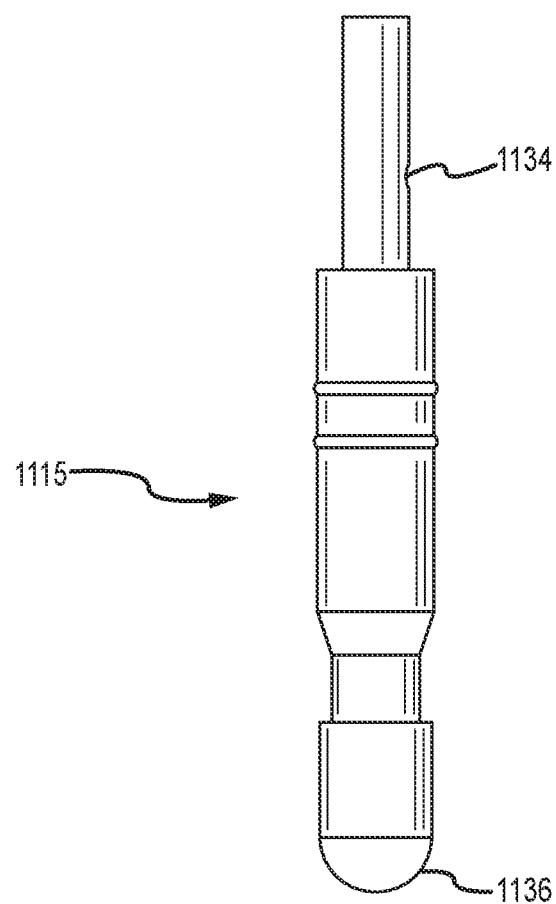
FIG. 15 is a top view of the plug in FIG. 14.
Figure 16:
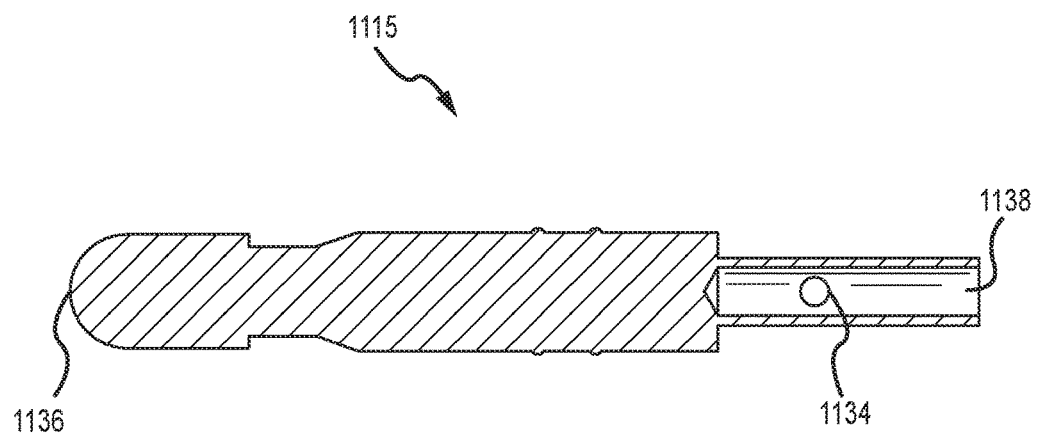
FIG. 16 is a side section view of the plug in FIG. 14.

FIGS. 14-16 illustrate details of a plug 1114 previously referenced herein. The plug 1114 may have one or more raised surfaces providing a housing engagement mechanism 1130 for a friction fit between the plug and an interior surface 1148 (see e.g. FIG. 19) of a passage 1140 in the housing body 1128. The plug 1114 or plug body 1124 may also have a transverse passage or recess 1134 for receiving a set pin or other elongated member (not illustrated) so as to affix a wire 108 (not illustrated) in a longitudinal recess 1138 (see FIG. 16) at a distal portion of the plug 1114 or plug body 1124.

Continuing with FIG. 16, a proximal portion of the plug body 1124 may have a tapered or curved surface 1136 to facilitate entry into a receptacle 1154 (FIG. 20) in the socket 1112 and engagement with the socket 1112.

Figure 17:
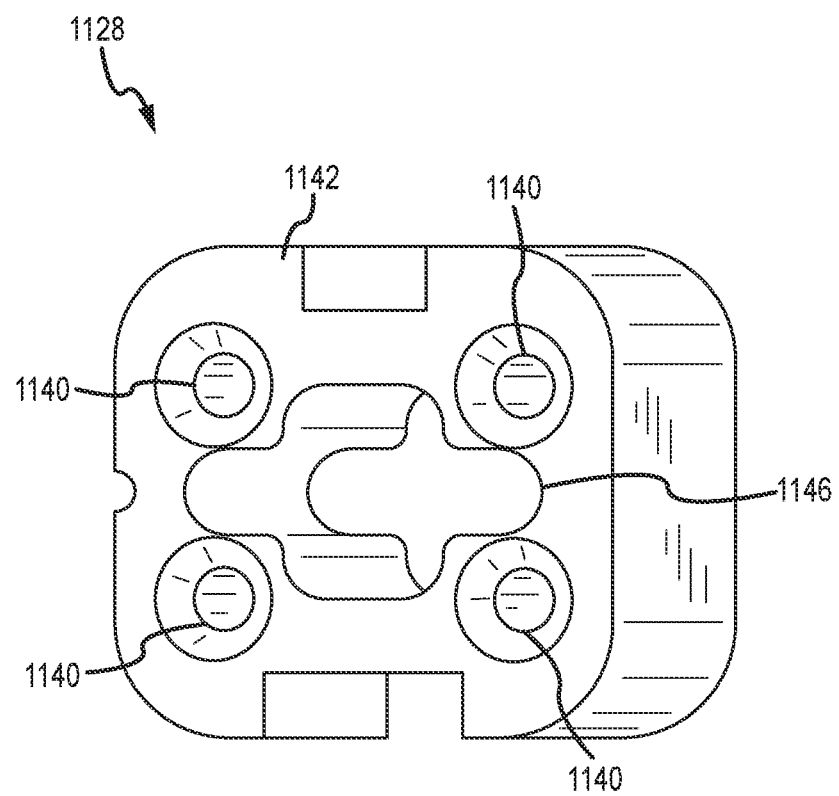
FIG. 17 is a distal perspective view of a housing suitable for use in the instrument in FIG. 11.
Figure 18:
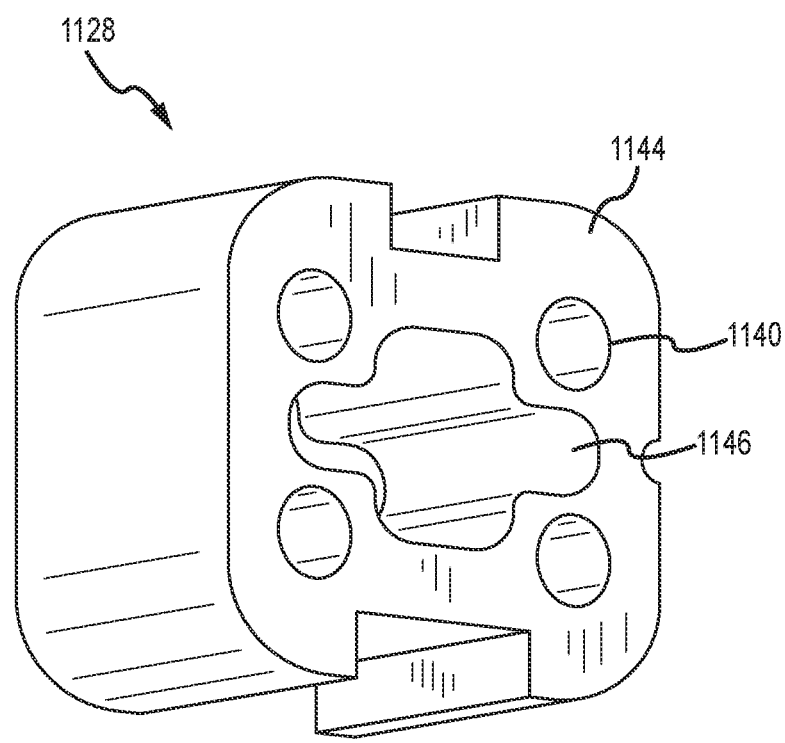
FIG. 18 is a proximal perspective view of the housing in FIG. 17.
Figure 19:
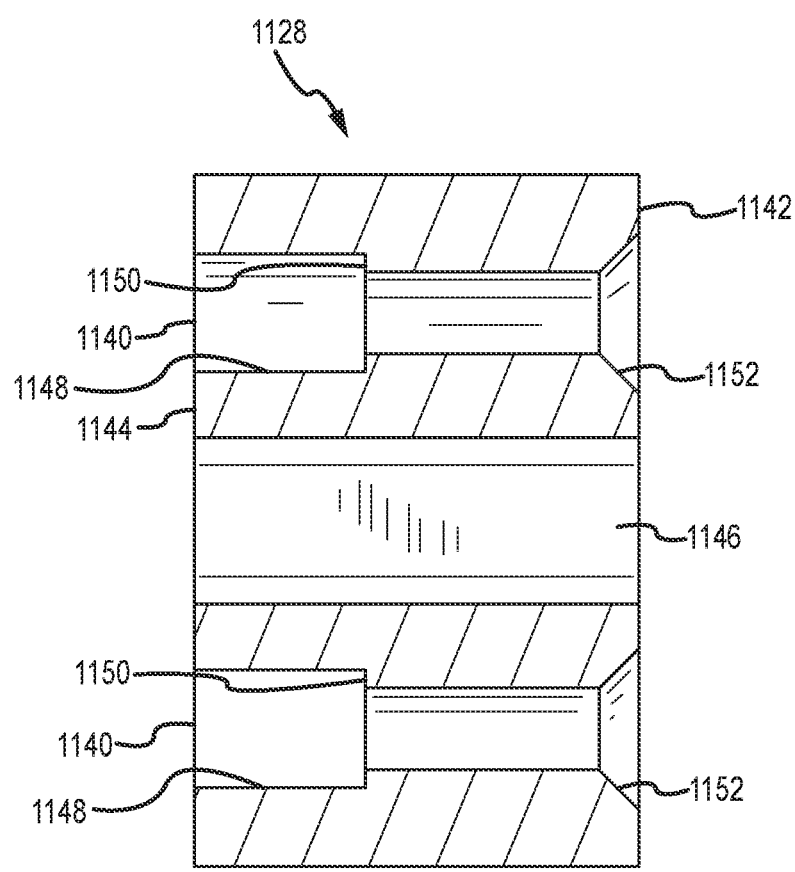
FIG. 19 is a side section view of the housing in FIG. 17.

As illustrated in FIGS. 17-19, the housing 1116 or body 1128 may have a plurality of passages 1140 to retain the plugs 1112. The passages 1140 may extend longitudinally from a first or proximal surface 1144 to a second or distal surface 1142 of the body 1128. The passages 1140 may have a relief or tapered entry 1152 to facilitate alignment of the connector housing 1116 or coupling system 1100 with other components of a tissue removal system and/or to reduce or eliminate the likelihood of wires 108 (not illustrated) being crimped as they exit the coupling system 1110.

With continued reference to FIGS. 17-19, the passages 1140 may have an interior surface 1148 that is sized and shaped to as to ensure a friction fit with the plugs 1114. The passages 1140 may also have a flanged surface 1150 positioned to engage respective flanged surfaces 1132 on the plugs 1114 to prevent the plugs 1114 from be pulled or pushed distally from the housing 1116 or body 1128.

Another passage 1146 (see e.g. FIG. 18) may provide an alignment feature between the connector bodies 1128, 1120 and/or provide a recess for passing other tool components through the coupling system 1100. The passage 1146 may also be used to align and hold the connector body 1128 to the instrument 1100 with a mating feature on the distal end of the instrument 1100 or the tray 1106 that retains the connector body 1120 with a friction fit.

FIGS. 20-23 illustrate details of the sockets 1112. One or more of sockets 1112 may be provided, having a body 1120 with a plug retaining mechanism 1122 positioned in a plug receptacle 1154 for retaining a plug 1114 therein. Those skilled in the art will recognize that the plug retaining mechanism 1122 may be a resilient member 1168 (see e.g. FIG. 23) having an inwardly-facing resilient protrusion 1166 for engaging a recess or socket engagement mechanism 1126 in the plug 1114. The resilient member 1168 may be positioned in the recess 1154 and held in place by flanged surfaces 1162, 1164 (see e.g. FIG. 22). Those skilled in the art will recognize numerous means of providing a plug-socket engagement.

As previously described herein, the proximal end of the socket(s) 1112 may have a tensioning coupling mechanism 1156 for engaging the tensioning mechanism 1108. The coupling mechanism 1156 may include a recess or groove for receiving a portion of the tensioning mechanism 1108 and another recess for receiving a screw or other elongated member for fastening the socket 1112 or socket body 1120 to the tensioning mechanism 1108.

Figure 24:
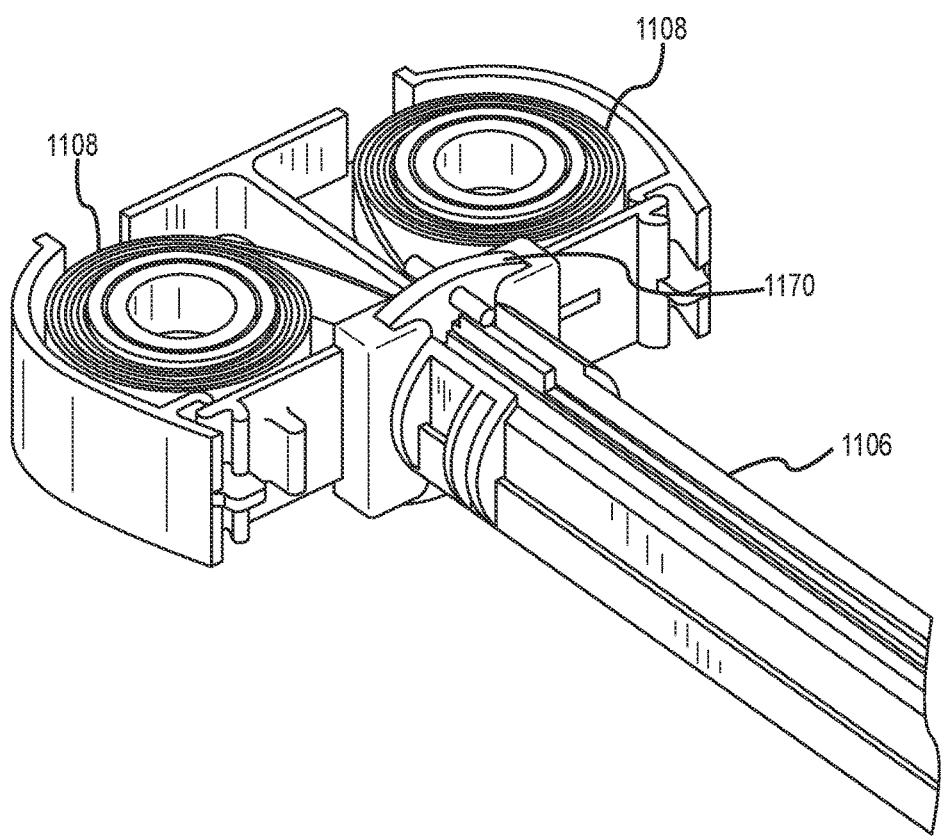
FIG. 24 is a top perspective view of details of the instrument in FIG. 11.
Figure 25:
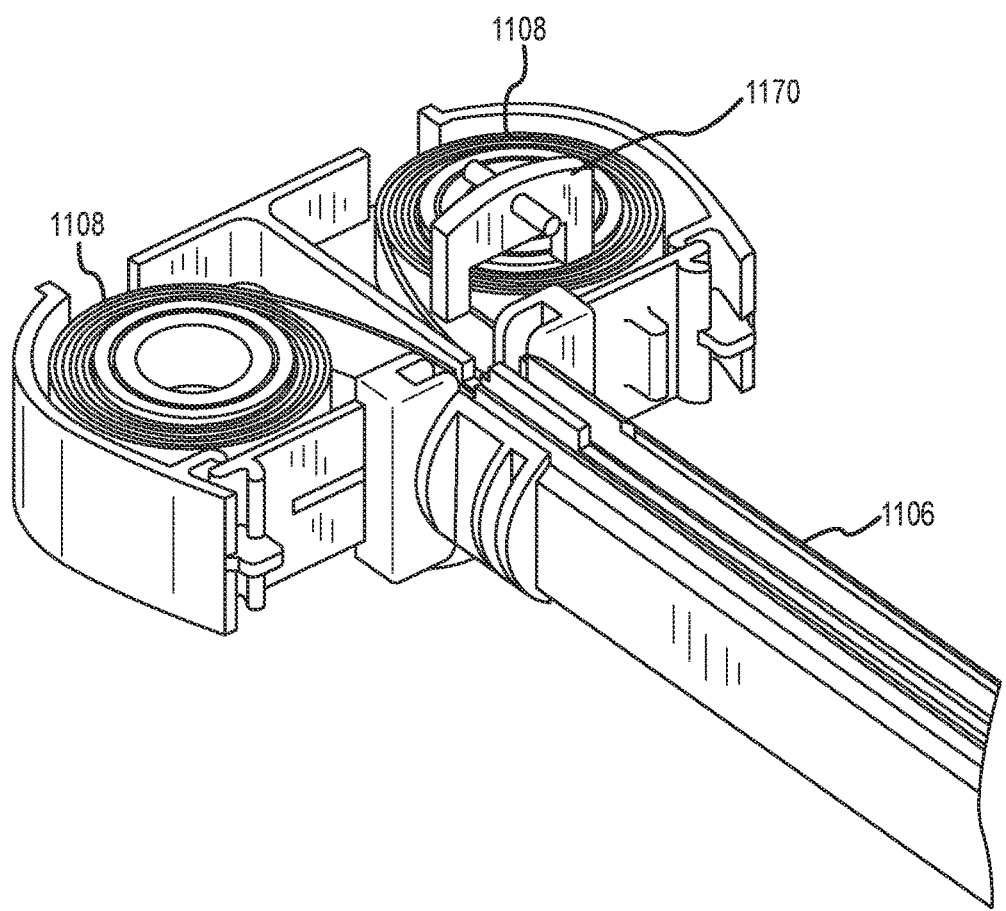
FIG. 25 is a bottom perspective view of details of the instrument in FIG. 11.
Figure 26:
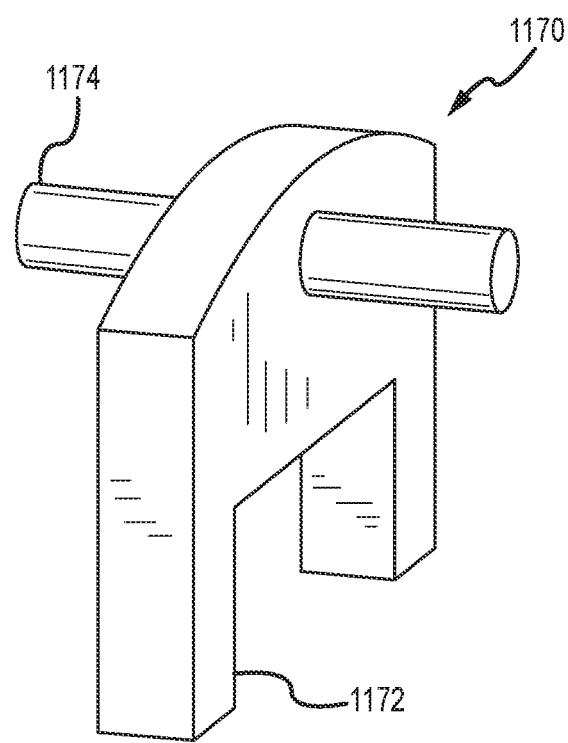
FIG. 26 is a perspective view of an actuation mechanism suitable for use in the instrument in FIG. 11.

With reference now to FIGS. 24-26, the tray 1106 may house one or more (e.g. four, as illustrated) tensioning mechanisms 1108. The tray 1106 may also house one or more release mechanisms 1170 for selectively releasing the spring-biased tensioning mechanisms 1108. In the embodiment illustrated, the release mechanism 1170 includes two bodies, each having an alignment mechanism 1172 to limit the release mechanism 1170 to sliding motion relative to the tray 1106 and an actuation mechanism 1174 to move the release mechanism 1170. In the embodiment illustrated, two tensioning mechanisms 1108 are operated by each release mechanism 1170, although those skilled in the art will recognize that any number of tensioning mechanisms 1108 and release mechanisms 1170 may be provided so as to control the movement of any number of plugs 1114 and wires 108.

As previously alluded, the instrument 1100 and coupling system 1110 illustrated in FIGS. 11-26 may, unless otherwise explicitly stated, generally have and/or be compatible with the features of the device 100 and coupling system 700 previously described herein.

Figure 27:
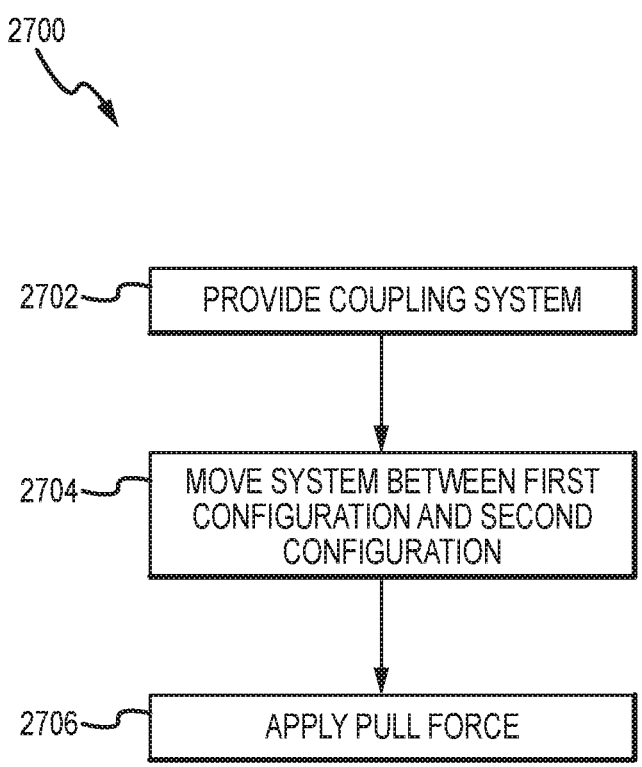
FIG. 27 is a flowchart of a method.

Turning now to FIG. 27, a method 2700 having one or more steps is described. The method 2702 may include providing 2702 a coupling system, the coupling system having a first plug detachably coupled to a first housing, and a first socket detachably coupled to a second housing, the first socket configured to receive the first plug.

The method 2702 may include moving 2704 the coupling system between a first configuration wherein the first and second housings are not engaged and a second configuration wherein the first and second housings are engaged and the first plug and the first socket are coupled together.

The method 2700 may include applying 2706 a pulling force on one of the first plug or the first socket to cause the first plug and the first socket to slide relative to the first and second housings. Applying 2706 a pulling force may be performed when the coupling system is in the second configuration.

The method 2700 may be performed using the coupling system 700, 1110 or instrument 100, 1100 previously described herein.

Embodiments of the invention can be embodied in a variety of ways. In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "biasing member" should be understood to encompass disclosure of the act of "biasing"—whether explicitly discussed or not—and, conversely, were there only disclosure of the act of "biasing", such a disclosure should be understood to encompass disclosure of a "biasing mechanism". Such changes and alternative terms are to be understood to be explicitly included in the description.

In conclusion, the present invention provides, among other things, a system and method for coupling. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A coupling system, comprising:
a first plug detachably coupled to a first housing; and
a first socket detachably coupled to a second housing, the first socket configured to receive the first plug; wherein the system is movable between a first configuration wherein the first and second housings are not engaged and a second configuration wherein the first and second housings are engaged and the first plug and the first socket are coupled together; and wherein when the system is in the second configuration, the first plug and the first socket are slidable relative to the first and second housings.

2. The system of claim 1, further comprising:
a retaining mechanism for locking the first and second housings in the second configuration.

3. The system of claim 2, wherein:
the retaining mechanism comprises a lock member in one of the first housing or the second housing and a catch in the other one of the first housing or the second housing, the lock member and the catch configured to selectively maintain the first and second housing in the second configuration.

4. The coupling system of claim 1, wherein:
when the system is in the first configuration, the first plug is fixed relative to the first housing and the first socket is fixed relative to the second housing.

5. The coupling system of claim 1, wherein:
when the system is in the first configuration, the first plug is fixed relative to the first housing and the first socket is fixed relative to the second housing.

6. The coupling system of claim 1, wherein:
when the system is in the first configuration, the first plug is fixed to the first housing by a friction fit, and the first socket is fixed to the second housing by a friction fit;
when the system is in the second configuration, the first plug and the first socket are slidable relative to the first and second housings by application of a pulling force that is greater than a retaining force applied by the friction fits of the first plug and first socket.

7. The coupling system of claim 1, wherein:
when the system is in the second configuration, the first plug and the first socket are coupled together by a detent engagement.

8. The coupling system of claim 1, wherein:
the first housing and the second housing are substantially electrically non-conductive; and
the first plug and the first socket are electrically conductive.

9. The coupling system of claim 1, further comprising:
a second plug; and
a second socket configured to receive the second plug.

10. The coupling system of claim 1, further comprising:
an alignment mechanism configured to align the first plug and the first socket.

11. The coupling system of claim 1, wherein:
the first plug has a first end for engagement with a wire electrode and a second end for engagement with the first socket.

12. The coupling system of claim 1, wherein:
the first socket has a first end for receiving the first plug and a second end for engagement with a tensioning mechanism.

13. An instrument, comprising:
an actuation tool having a tensioning mechanism;
at least one wire; and
a coupling system for coupling the tensioning mechanism and the wire, the coupling system having a first plug detachably coupled to a first housing, and a first socket detachably coupled to a second housing, the first socket configured to receive the first plug, wherein the coupling system is movable between a first configuration wherein the first and second housings are not engaged and a second configuration wherein the first and second housings are engaged and the first plug and the first socket are coupled together; and wherein
the first plug or the first socket is coupled to the at least one wire; and
the other one of the first plug or the first socket is coupled to the tensioning mechanism.

14. The instrument of claim 13, wherein:
when the coupling system is in the second configuration, the first plug and the first socket are slidable relative to the first and second housings.

15. The instrument of claim 14, wherein:
when the coupling system is in the first configuration, the first plug is fixed relative to the first housing and the first socket is fixed relative to the second housing.

16. The instrument of claim 13, wherein:
when the coupling system is in the first configuration, the first plug is fixed relative to the first housing and the first socket is fixed relative to the second housing.

17. The instrument of claim 13, wherein:
when the coupling system is in the first configuration, the first plug is fixed to the first housing by a friction fit, and the first socket is fixed to the second housing by a friction fit;
when the coupling system is in the second configuration, the first plug and the first socket are slidable relative to the first and second housings by application of a pulling force that is greater than a retaining force applied by the friction fits of the first plug and first socket.

18. The instrument of claim 13, wherein:
when the coupling system is in the second configuration, the first plug and the first socket are coupled together by a detent engagement.

19. The instrument of claim 13, further comprising:
a second plug; and
a second socket configured to receive the second plug.

20. The instrument of claim 13, wherein:
the at least one wire is an electrically conductive electrode wire; and
the first and second housings are substantially electrically non-conductive.

21. A method, comprising:
providing a coupling system, the coupling system having a first plug detachably coupled to a first housing, and a first socket detachably coupled to a second housing, the first socket configured to receive the first plug; and
moving the coupling system between a first configuration wherein the first and second housings are not engaged and a second configuration wherein the first and second housings are engaged and the first plug and the first socket are coupled together, wherein when the coupling system is in the second configuration, applying a pulling force on one of the first plug or the first socket to cause the first plug and the first socket to slide relative to the first and second housings.

\* \* \* \* \*